(12) United States Patent
Minoz et al.

(10) Patent No.: US 8,653,444 B2
(45) Date of Patent: Feb. 18, 2014

(54) CALIBRATION METHOD

(75) Inventors: Alain Minoz, Bromma (SE); Gunnar Backman, Segeltorp (SE)

(73) Assignee: Elekta AB (Publ), Stockholm (SE)

( * ) Notice: Subject to any disclaimer, the term of this patent is extended or adjusted under 35 U.S.C. 154(b) by 161 days.

(21) Appl. No.: 13/120,136

(22) PCT Filed: Sep. 22, 2008

(86) PCT No.: PCT/EP2008/062644
§ 371 (c)(1),
(2), (4) Date: May 4, 2011

(87) PCT Pub. No.: WO2010/031452
PCT Pub. Date: Mar. 25, 2010

(65) Prior Publication Data
US 2011/0272568 A1    Nov. 10, 2011

(51) Int. Cl.
*G01D 18/00*    (2006.01)
*G12B 13/00*    (2006.01)

(52) U.S. Cl.
USPC .................................. 250/252.1; 250/370.14

(58) Field of Classification Search
USPC ......................................... 250/252.1, 370.14
See application file for complete search history.

(56) References Cited

U.S. PATENT DOCUMENTS

| 4,780,898 A | 10/1988 | Sundqvist |
| 7,186,981 B2 * | 3/2007 | Shepard et al. ............ 250/341.1 |
| 7,489,402 B2 * | 2/2009 | Selker et al. .................. 356/417 |
| 2005/0109939 A1 | 5/2005 | Engler et al. |

FOREIGN PATENT DOCUMENTS

| WO | WO 91/03745 A1 | 3/1991 |
| WO | WO 2004/006269 A1 | 1/2004 |
| WO | WO 2008/098591 A1 | 8/2008 |

* cited by examiner

*Primary Examiner* — David Porta
*Assistant Examiner* — Abra Fein
(74) *Attorney, Agent, or Firm* — Birch, Stewart, Kolasch & Birch, LLP

(57) ABSTRACT

A method and a calibration system for calibrating a measurement tool for measuring the radiation in a radiation system, such as a radiation therapy system, are provided. The measurement tool, including a holder and at least one photodiode element, is adapted to be mounted in a positioning unit of the radiation system. The radiation sensitive volume of the photodiode element is embedded in a light transparent coating transparent for, for instance, light in the visible spectrum. Thereby, the position of the sensitive volume can easily be determined or calculated with high accuracy relative to the holder on which the photodiode element is arranged, from which the position of the sensitive volume can be determined or calculated in relation to the positioning unit of the radiation system.

19 Claims, 5 Drawing Sheets

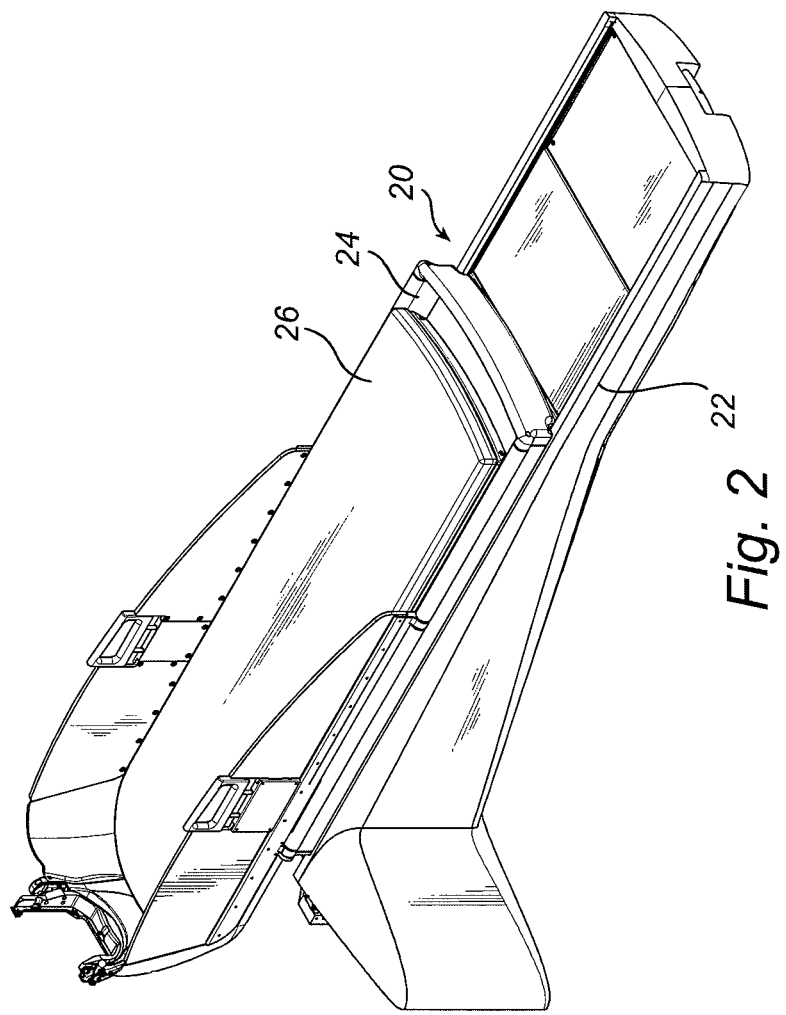
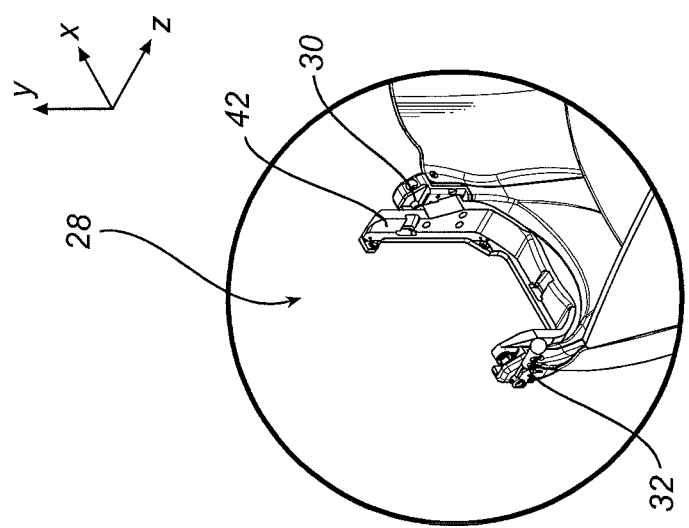
Fig. 2
Fig. 3

CALIBRATION METHOD

FIELD OF THE INVENTION

The present invention relates to the field of radiation therapy. In particular, the invention concerns a method for calibrating a measurement tool for measuring the radiation in a radiation system such as a radiation therapy system, a measurement tool for such a method, and a calibration system for calibrating a measurement tool.

BACKGROUND OF THE INVENTION

The development of surgical techniques has made great progress over the years. For instance, for patients requiring brain surgery, non-invasive surgery is now available which is afflicted with very little trauma to the patient.

Stereotactic radiosurgery is such a minimally invasive treatment modality that allows delivery of a large single dose of radiation to a specific intracranial target while sparing surrounding tissue. Unlike conventional fractionated radiotherapy, stereotactic radiosurgery does not rely on, or exploit, the higher radiosensitivity of neoplastic lesions relative to normal brain (therapeutic ratio). Its selective destruction depends primarily on sharply focused high-dose radiation and a steep dose gradient away from the defined target. The biological effect is irreparable cellular damage and delayed vascular occlusion within the high-dose target volume. Because a therapeutic ratio is not required, traditionally radioresistant lesions can be treated. Because destructive doses are used, however, any normal structure included in the target volume is subject to damage.

One such non-invasive radiotherapy technique is so called LINAC (Linear Accelerator) radio therapy. In a LINAC radiotherapy system, a collimated x-ray beam is focused on a stereotactically identified intracranial target. In such an accelerator, electrons are accelerated to near light speed and are collided with a heavy metal, e.g. tungsten. The collision mainly produces heat but a small percentage of the energy is converted into highly energetic photons, which, because they are electrically produced, are called "x-rays". The gantry of the LINAC rotates around the patient, producing an arc of radiation focused on the target. The couch in which the patient rests is then rotated in the horizontal plane, and another arc is performed. In this manner, multiple non-coplanar arcs of radiation intersect at the target volume and produce a high target dose, resulting in a minimal radiation affecting the surrounding brain. The x-rays are normally created by accelerating electrons to near light speed, and then colliding them with a heavy metal (e.g., tungsten). The collision mainly produces heat but a small percentage of the energy is converted to highly energetic protons, which are collimated and focused on the target.

Another system for non-invasive surgery is commercially available under the name of Leksell Gamma Knife®, which provides such surgery by means of gamma radiation. The radiation is emitted from a large number of fixed radioactive sources and is focused by means of collimators, i.e. passages or channels for obtaining a beam of limited cross section, towards a defined target or treatment volume. Each of the sources provides a dose of gamma radiation which is insufficient to damage intervening tissue. However, tissue destruction occurs where the radiation beams from all radiation sources intersect or converge, causing the radiation to reach tissue-destructive levels. The point of convergence is hereinafter referred to as the "focus point". Such a gamma radiation device is referred to and described in U.S. Pat. No. 4,780,898.

In the system, the head of a patient is immobilized in a stereotactic instrument which defines the location of the treatment volume in the head. Further, the patient is secured in a patient positioning system which moves the entire patient so as to position the treatment volume in coincidence with the focus point of the radiation unit of the system.

Consequently, in radiotherapy systems, such as a LINAC system or a Leksell Gamma Knife® system, it is of a high importance that the positioning system which moves the patient so as to position the treatment volume in coincidence with the focus point of the radiation unit of the system is accurate and reliable. That is, the positioning system must be capable of positioning the treatment volume in coincidence with the focus point at a very high precision. Furthermore, this high precision must also be maintained over time.

A predetermined position of a positioning system in a radiation therapy system comprising a radiation therapy unit can be determined relative to a fixed radiation focus point of the radiation therapy unit by radiation measurements, e.g., using a phantom with radiation sensitive film provided in a certain position within the phantom. Another method is applying a radiation sensitive film on a tool adapted to be mounted in the positioning system, which tool is provided with reference marks such that it can be mounted in a defined position relative to the positioning system. According to a further method, a phantom with an ionization chamber provided in a certain position within the phantom is used. However, these indirect methods are time-consuming and inaccurate.

In accordance with a further method, a PN diode (or PN diodes) mounted on a measurement tool, providing an output that is substantially proportional to the detected radiation, is used to determine a predetermined position of the positioning system relative to a fixed radiation focus point. The signal from the diode is amplified and measured. The diode or diodes are scanned over the stationary focus point of the radiation unit of the radiation therapy system. Measurement values regarding the coordinates of the positioning system are collected or obtained where a gradient of the radiation is high, i.e. at the edges of the radiation curve.

However, the measurement tool must itself be calibrated, which is conducted in a master system. The master system has, in turn, been calibrated by means of film measurements. Hence, in order to verify the predetermined position of a positioning system of a radiation therapy system, a measurement tool that has been calibrated in another radiation therapy system, the master system, is used. Even if the master system has been calibrated using film measurements, a certain degree of inaccuracy will remain. Further, in order to calibrate the measurement tool, access to the master system is required, which may be a limited resource in terms of accessibility, and the calibration has to be performed by specially trained personnel.

Thus, there is a need for an efficient and reliable method for calibrating a measurement tool for measuring the radiation in a radiation system such as a radiation therapy system. Thereby, an efficient and reliable determination or verification of a predetermined position of the positioning system in a radiation therapy system comprising a radiation therapy unit relative to a fixed radiation focus point of the radiation therapy unit can be achieved.

SUMMARY OF THE INVENTION

One object of the present invention is to provide an efficient and reliable method for calibrating a measurement tool for measuring the radiation in a radiation system such as a radiation therapy system.

This and other objects are achieved by providing a calibration method, a calibration system, and a measurement tool having the features as defined in the independent claims. Preferred embodiments of the invention are defined in the dependent claims.

As used herein, the term "measurement tool" refers to a unit for holding at least one photodiode element, which preferably is a diode surface-mounted on a circuit board or some other suitable support apparent for a person skilled in the art. The measurement tool is, according to an embodiment, adapted to be mounted in fixed engagement with fixation unit, which, in turn, is adapted to be mounted in fixed engagement with the positioning system or positioning unit. In an alternative embodiment, the measurement tool is adapted to be mounted in fixed engagement in the exact same position as the fixation unit used for fixation of a patient, or rather for a portion of the patient containing a tissue region to be treated.

The present invention is based on the idea of using optical photodiodes, or photodiodes, in a measurement tool for measuring the radiation of a radiation system such as a radiation therapy system. Preferably, the measurement tool is adapted to be mounted in a positioning unit of the radiation system. The radiation sensitive volume of an optical photodiode is embedded in a light transparent coating that is transparent for, inter alia, light in the visible spectrum. Thereby, the position (i.e. the coordinates) of the sensitive volume can easily be determined or calculated with high accuracy relative to, for example, a circuit board on which the photodiode is arranged, and hence, according to a preferred embodiment of the invention, the position of the sensitive volume can easily be determined or calculated in relation to the positioning unit of the radiation system.

The coordinates of the fixation unit are defined by a fixation unit coordinate system, which through the fixed relationship with the treatment volume also is used for defining the outlines of the treatment volume. In operation, the fixation unit, and hence the fixation unit coordinate system, is moved in relation to the fixed radiation focus point such that the focus point is accurately positioned in the intended coordinate of the fixation unit coordinate system. The measurement tool may thus use the same coordinate system, i.e. the fixation unit coordinate system.

Examples of a fixation unit and coordinate system include the Leksell stereotactic head frame and the Leksell XYZ coordinate system, respectively. The Leksell XYZ coordinate system is a Cartesian coordinate system defined by three orthogonal axes perfectly aligned with the frame of a fixation unit, which is arranged with three orthogonal sides. In relation to a patient, the x-axis extends in the medial-lateral direction of the patient, the y-axis extends in the anterior-posterior direction, and the z-axis extends in the cranial-caudal direction. In other words, if a patient is properly positioned in the Leksell XYZ coordinate system, the x-axis would run from ear to ear, the z-axis from head to toe, and the y-axis from back to front of the patient. However, it should be noted that other coordinate systems for defining the volume fixed by the fixation unit, as well as other types of fixation units could be used without departing from the scope of the claimed invention.

The measurement tool for holding the optical diode elements is preferably provided with at least one engagement point for mounting the measurement tool at a fixation arrangement, which, in turn, can be mounted in at least one corresponding engagement point provided in the positioning system or unit. When mounted, the measurement tool is in fixed engagement with the patient positioning unit and cannot be translated or rotated in relation to the positioning unit. For this purpose, a plurality of engagement points are preferably used for facilitating the rotational or angular fixation. However, one fixation point locking the angular and translational relationship between the measurement tool and the positioning unit is also contemplated within the scope of the invention.

Irrespective of whether one or several points of engagement between the measurement tool and the patient positioning unit are used, the engagement points of the engagement arrangement of the positioning unit can be manufactured with a very high accuracy and without any play or backlash to the measurement tool. In other words, the fixation of the measurement tool to the patient positioning unit has a very high positioning accuracy reproducibility. Thereby, the relationship between the measurement tool coordinate system and the engagement points of the measurement tool, and hence of the positioning unit, can be determined and thus be known by the system.

According to a first aspect of the present invention, there is provided a method for calibrating a measurement tool, including at least one photodiode element, for measuring the radiation in a radiation system, which system comprises a radiation generating unit that is capable of focusing the radiation to a fixed radiation focus point, which method comprises the step of determining the coordinates for a sensitive volume of the at least one photodiode element relative to a reference of a diode element holder of the measurement tool.

According to a second aspect of the present invention, there is provided a system for calibrating a measurement tool for measuring the radiation in a radiation system, where the radiation system comprises a radiation generating unit that is capable of focusing the generated radiation to a fixed radiation focus point, wherein the calibration system includes a measurement tool, including at least one photodiode element, and a control unit that is adapted to calculate the coordinates for a sensitive volume of the at least one photodiode element relative to a reference of a diode element holder of the measurement tool.

According to a third aspect of the invention, there is provided a measurement tool for measuring the radiation in a radiation system, the measurement tool comprising a holder and at least one photodiode element arranged on the holder. Such a photodiode element has a radiation sensitive volume and is preferably embedded in a light transparent coating transparent for, inter alia, light in the visible spectrum.

According to an embodiment of the present invention, it is preferred to mount the measurement tool in the positioning unit, the positioning unit having a predetermined position relative to the radiation system, wherein the positioning unit is capable of moving the measurement tool along three substantially orthogonal axes, and calculate the coordinates for a sensitive volume of the at least one photodiode element. Furthermore, it is preferred to control movements of the positioning unit so as to position the positioning unit in at least one measurement position corresponding to the thus calculated coordinates for the at least one photodiode element, wherein the sensitive volume of the at least one photodiode element is located substantially at said fixed radiation focus point, and determine the position of the sensitive volume of the at least one photodiode element relative to the fixed radiation focus point for each of the at least one measurement position. Thus, the position (i.e. the coordinates) of the sensitive volume of the photodiode element or elements can in a simple manner be determined or calculated with high accuracy relative to the measurement tool on which the photodiode element or elements are arranged, and, hence, the position of the sensitive volume can easily be determined or calculated in relation to the positioning unit of the radiation system. In addition, the position of the sensitive volume of the photodiode element or elements are determined or calculated relative to the fixed radiation focus point.

According to an embodiment of the present invention, it is preferred that the determining of the position of the sensitive volume of the photodiode element relative to the fixed radiation focus point for each of the at least one measurement point further comprises determining, for each measurement position and for each axis of motion, whether there is a difference in the distance between the radiation focus point and the calculated coordinates for the sensitive volume of at least one photodiode element corresponding to said measurement position, and, for a given measurement position, if there is a difference for different axes of motion, storing the difference as a calibration value for said at least one photodiode element. Such calibration values can be used, for example, when performing a measurement session to determine a position of the patient positioning unit relative to the radiation focus point of another radiation system.

According to yet another embodiment of the present invention, it is preferred that the calculation of the coordinates for a sensitive volume of the at least one photodiode element further comprises determining a position for the holder for a diode element relative to the positioning unit.

According to yet another embodiment of the present invention, it is preferred that the determining of the position of the sensitive volume of the photodiode element relative to the fixed radiation focus point for each of the at least one measurement point further comprises determining, for each measurement position and for each axis of motion, whether there is a difference in the distance between the radiation focus point and the calculated coordinates for the at least one photodiode element corresponding to said measurement position, and, for a given measurement position, if there is a difference for different axes of motion, storing the difference as a calibration value for said at least one photodiode element. In addition, according to said embodiment of the present invention, the step of calculating the coordinates for a sensitive volume of the at least one photodiode element further comprises determining a position for the diode holder relative to the positioning unit.

According to another embodiment of the present invention, it is preferred that the mounting of the measurement tool further comprises mounting the measurement tool in a fixation arrangement, wherein the measurement tool is adapted to be fixedly mounted in said fixation arrangement, and mounting the fixation arrangement in the positioning unit. In this manner, the measurement tool cannot be displaced with respect to the positioning unit, thereby eliminating possible artifacts in the measurement of the radiation in the radiation system. This means that, after having used the calibrated measurement tool to determine a predetermined position of the positioning unit relative to a fixed radiation focus point, the risk of damaging tissue outside the treatment volume of a patient during radiotherapy is significantly lessened.

According to embodiments of the present invention, PiN diodes are used to measure the radiation.

According to an embodiment of the present invention, the control unit comprises storage means and the control unit is further adapted to, for each measurement point and for each direction of motion, determine whether there is a difference in distance between the radiation focus point and the calculated respective photodiode coordinate, and if there is a difference in distance in any of the directions of motion, store the difference as a calibration value for that photodiode element in the storage means. The storage means may be a portable storage means, such as an USB memory unit or a CD or a DVD, or a fixed storage means, such as a hard-disc drive, or any other suitable storage means apparent for a person skilled in the arts. Calibration values as described above can advantageously be used when performing a measurement session to determine a position of the patient positioning unit relative to the radiation focus point of another radiation system.

According to a further embodiment of the present invention, the measurement tool is adapted to be fixedly mounted in a fixation arrangement, and the fixation arrangement is adapted to be mounted in the patient positioning unit.

According to a further embodiment of the present invention, the calibration system comprises a fixation arrangement, and the positioning unit and the measurement tool each includes at least one engagement point. Furthermore, the fixation arrangement is adapted to be mounted in at least one engagement point corresponding to an engagement point in the positioning unit.

According to a further embodiment of the present invention, the measurement tool comprises at least two photodiode elements, arranged such that each of the photodiode elements is, when mounted in the positioning unit, situated in one of the planes defined by said three substantially orthogonal motional axes, and such that at least one photodiode element is situated in a first plane and at least one photodiode element is situated in a second plane of the planes defined by said three substantially orthogonal motional axes.

According to a further embodiment of the present invention, the measurement tool is rotatably mounted, so that the measurement tool is rotatable about at least one rotation axis. In this configuration, only one photodiode element is needed on the measurement tool in order to, in an arbitrary number of planes, as required, calculate the coordinates for a sensitive volume of the at least one photodiode element relative to the positioning unit.

According to a further embodiment of the present invention, the measurement tool is rotatably mounted, so that the measurement tool is rotatable about at least one rotation axis, wherein the at least one rotation axis is one of the three substantially orthogonal axes of motion.

According to an embodiment of the present invention, the holder of the measurement tool according to the third aspect of the invention is a printed circuit board. By using a printed circuit board as a holder for the one or more photodiode elements arranged thereon, electrical connection of the photodiode elements to a data processing means, a control unit, a processor, etc., can easily and compactly be carried out without the need for additional electrical wiring, etc.

According to another embodiments of the present invention, the measurement tool according to the third aspect of the invention is adapted to be used in a calibration system according to the second aspect of the invention or embodiments thereof, as defined herein and in the appended claims.

The present invention may also, as the skilled person realizes, be used to determine or measure the radiation in applications other than medical without any significant modifications, such as, for example, distance measuring systems where radiation is used to measure a distance to an object.

As a person skilled in the art realizes, the features of a particular embodiment of the invention described herein can be combined in an arbitrary manner with the features described with reference to other embodiments of the invention, as well as with the features disclosed in the appended claims, except in cases where it is stated otherwise, without departing from the scope of the invention.

BRIEF DESCRIPTION OF THE DRAWINGS

It should be understood that the exemplary embodiments of the present invention as shown in the figures are for illustrative purposes only. Further embodiments of the present invention will be made apparent when the figures are considered in conjunction with the following detailed description and the appended claims.

Furthermore, it is to be understood that the reference signs provided in the drawings are for the purpose of facilitating quicker understanding of the claims, and thus, they should not be construed as limiting the scope of the invention in any way.

FIG. 2 illustrates the positioning unit used in the calibration method of the present invention;

FIG. 3 illustrates a part of the positioning unit used in the calibration method of the present invention including the engagement points in more detail;

DESCRIPTION OF PREFERRED EMBODIMENTS

Preferred embodiments of the present invention will now be described for the purpose of exemplification with reference to the accompanying drawings, wherein like numerals indicate the same elements throughout the views. It should be understood that the present invention encompasses other exemplary embodiments that comprise combinations of features described in the following. Additionally, other exemplary embodiments of the present invention are defined in the appended claims.

Figure 1:
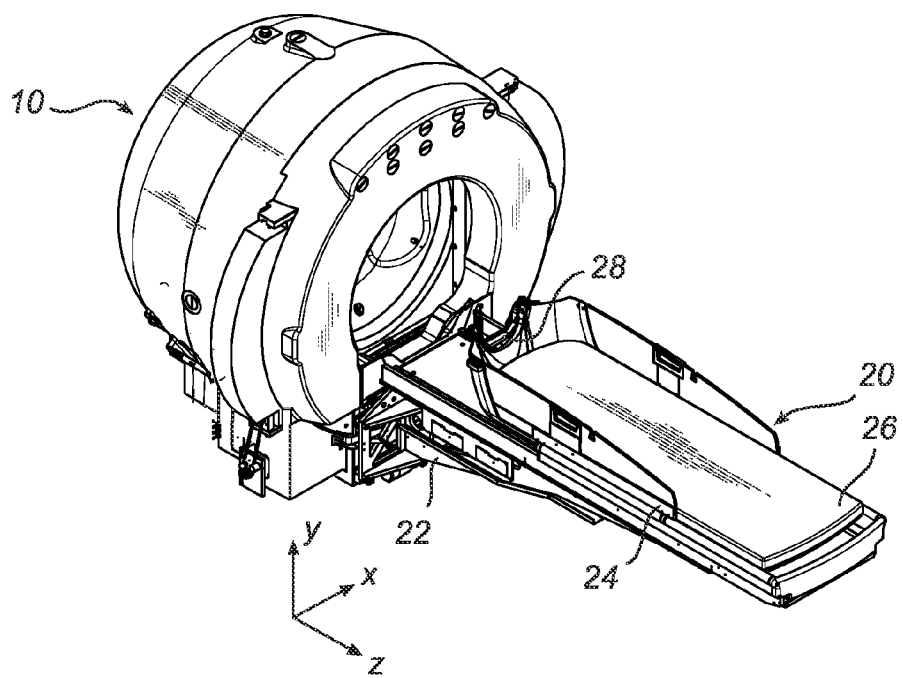
FIG. 1 illustrates the general principle of a radiation therapy system in which the present invention may be used.

With reference to FIGS. 1-3, a radiation therapy system for which the present invention is applicable comprises a radiation unit 10 and a patient positioning unit 20. In the radiation unit 10, there are provided radioactive sources, radioactive source holders, a collimator body, and external shielding elements. The collimator body comprises a large number of collimator channels directed towards a common focus point, in a manner commonly known in the art.

The collimator body also acts as a radiation shield preventing radiation from reaching the patient other than through the collimator channels. Examples of collimator arrangements in radiation therapy systems applicable to the present invention can be found in WO 2004/06269 A1, which is hereby incorporated herein by reference in its entirety. However, the present invention is also applicable to radiation therapy systems using other arrangements for collimating radiation into a fixed focus point, such as is disclosed in U.S. Pat. No. 4,780,898. Furthermore, the present invention is also applicable to LINAC radiosurgical systems, in which a collimated x-ray beam is focused on a stereotactically identified intracranial target and the gantry of the LINAC rotates around the patient, producing an arc of radiation focused on the target. In addition, the present invention is also applicable in other radiation systems, for example, systems where radiation is used to determine a distance to an object.

Figure 4:
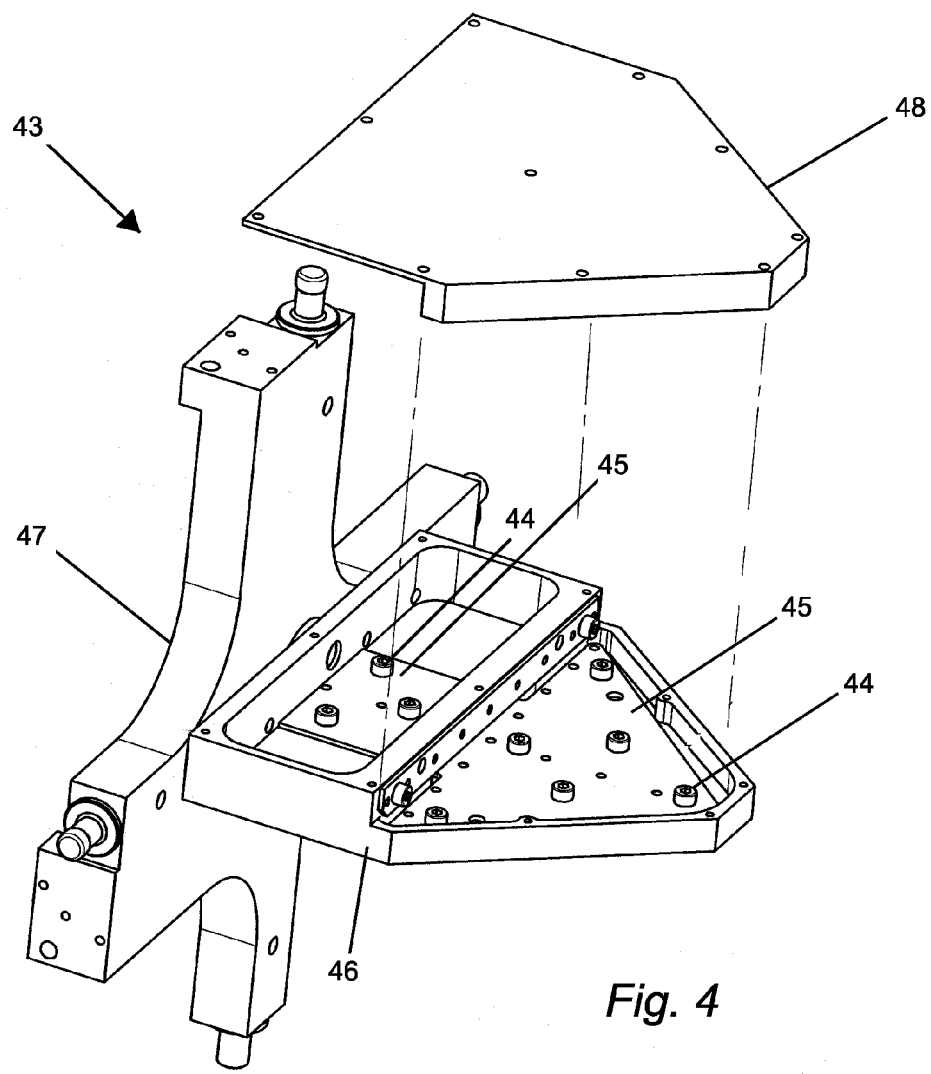
FIG. 4 illustrates the measurement tool according to an exemplary embodiment of the present invention.

The patient positioning unit 20 comprises a rigid framework 22, a slidable or movable carriage 24, and motors (not shown) for moving the carriage 24 in relation to the framework 22. The carriage 24 is further provided with a patient bed 26 for carrying and moving the entire patient. At one end of the carriage 24, there is provided a fixation arrangement 28 for receiving and fixing a patient fixation unit, either directly or via an adapter unit 42. According to an embodiment of the present invention, a measurement tool 43 (FIG. 4) including one or more photodiode elements 44, which measurement tool 43 preferably is one or more photodiodes 44 surface-mounted on a printed circuit board 45, is adapted to be mounted in fixed engagement with the positioning unit 20 in the exact same position as the fixation unit used for fixation of a patient, or rather for a portion of the patient containing the treatment volume, that is the tissue region that is to be treated. An exemplary embodiment of the measurement tool 43 is illustrated in FIG. 4. In the illustrated embodiment, the measurement tool 43 includes a base 46 for holding one or more printed circuit boards 45 on which a plurality of photodiodes 44 are arranged, with the measurement tool 43 being rigidly coupled to the positioning unit 20 via a frame 47. In the exemplary embodiment illustrated in FIG. 4, the printed circuit boards 45 are arranged such that each of the printed circuit boards 45 is parallel with one of the xy or xz planes defined in FIG. 1. As illustrated in FIG. 4, a plurality of photodiodes 44 are arranged on the printed circuit boards 45 in a row and in an array. However, it is to be understood that many different arrangements of the photodiodes 44 on the printed circuit boards 45, including, but not limited to, the ones shown in FIG. 4, may be contemplated without departing from the scope of the invention. As illustrated in FIG. 4, a protective cover 48 may be used during periods of not using the measurement tool 43 in order to protect the photodiodes 44 from being exposed to ambient light.

According to a further embodiment (not shown), the measurement tool is arranged such that the holder, preferably a printed circuit board, can be rotated about at least one axis of rotation. In one exemplary embodiment, the axis of rotation coincides with the x axis defined in FIG. 1.

The coordinates of the fixation unit is defined by a fixation unit coordinate system, which through the fixed relationship with the treatment volume also is used for defining the outlines of the treatment volume. In operation, the fixation unit, and hence the fixation unit coordinate system, is moved in relation to the fixed radiation focus point such that the focus point is accurately positioned in the intended coordinate of the fixation unit coordinate system. The measurement tool may thus use the same coordinate system, i.e. the fixation unit coordinate system.

According to the illustrated embodiment in FIG. 3, the fixation arrangement 28 comprises two engagement points 30, 32, which are arranged for preventing the patient fixation unit from translational and/or rotational movement in relation to the movable carriage 24.

Figure 5A:
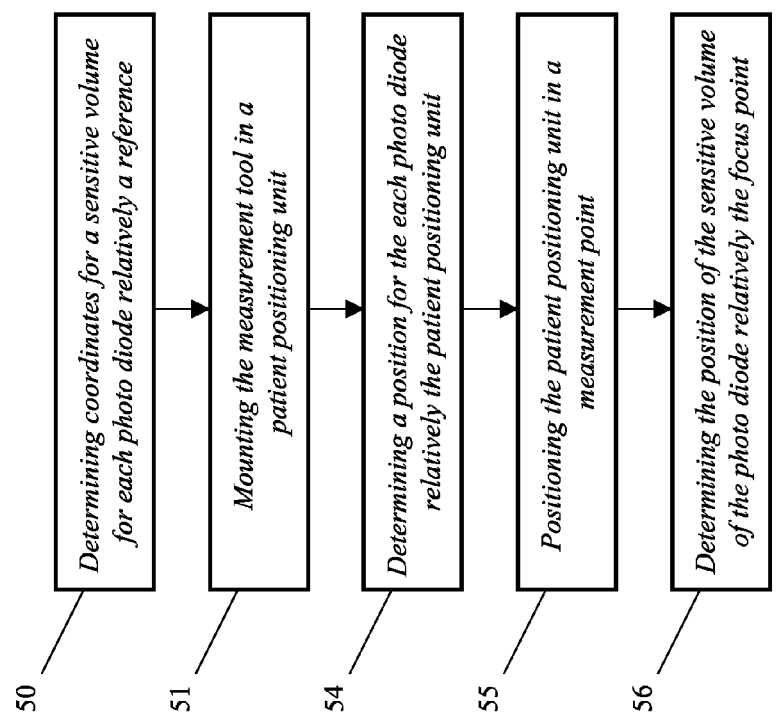
FIGS. 5A-5B are flowcharts illustrating the calibration method according to exemplary embodiments of the present invention.
Figure 5B:
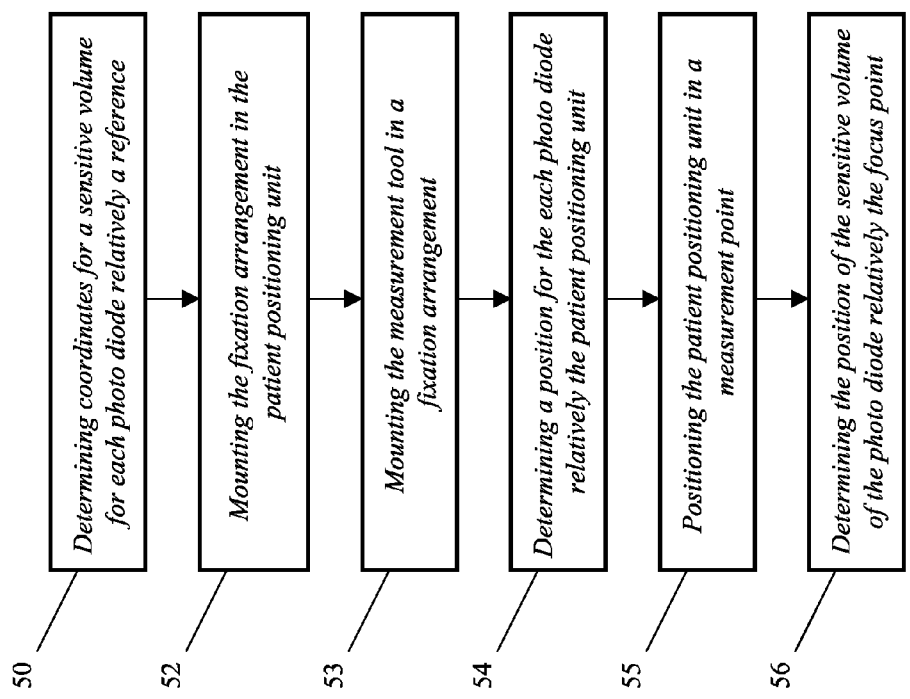

FIGS. 5A-5B schematically illustrate two preferred, albeit exemplary, embodiments of the calibration method according to the present invention for calibrating a measurement tool for measuring the radiation in a radiation system. The illustrated embodiments relate to a stereotactic radio therapy system for providing gamma radiation therapy to a target volume in the head of human patient.

The step 50 comprises, for each of the photodiode elements, such as photodiodes, being mounted on the measurement tool, determining the coordinates for a (radiation) sensitive volume of the photodiode relative to a reference of a holder for a diode element of the measurement tool.

Next, according to the exemplary embodiment of the invention illustrated in FIG. 5A, the measurement tool is mounted in the patient positioning unit (step 51). The patient positioning unit is adapted so that it can be moved along the three axes x, y, and z defined in FIG. 1. Alternatively, according to the exemplary embodiment of the invention illustrated in FIG. 5B, as shown in steps 52 and 53, the measurement tool is mounted in a fixation arrangement, such as the Leksell stereotactic head frame. Advantageously, the measurement tool is arranged such that it is adapted to be fixedly mounted in such a fixation arrangement. Next, the fixation arrangement is mounted in the patient positioning unit. Preferably, the patient positioning unit has a predetermined position relative to the radiation system. The patient positioning unit is adapted so that it can be moved along the three axes x, y, and z defined in FIG. 1.

Thereafter, step 54 is performed, which comprises determining a position (that is, the coordinates) of the diode element holder relative to the patient positioning unit.

Next, in step 55, the patient positioning unit is moved such that the positioning unit is positioned in at least one measurement point that corresponds to the calculated photodiode coordinates for a photodiode, as calculated in step 50, and such that the sensitive volume of the photodiode is located substantially at the focus point for the radiation system.

Finally, in step 56, the position of the sensitive volume of the photodiode relative to the focus point in each measurement point is determined.

As already discussed, the present invention is based on the idea of using optical diodes, or photodiodes, in the measurement tool for measuring the radiation of a radiation system such as a radiation therapy system. Preferably, the radiation sensitive volume of an optical diode is embedded in a light transparent coating transparent for, for instance, light in the visible spectrum. Thereby, the coordinates of the sensitive volume of the photodiode can easily be determined or calculated with high accuracy, relative to the circuit board or the like on which the diode is arranged, and, thus, the position of the sensitive volume can easily be determined or calculated relative to the patient positioning unit.

Consequently, the present invention considerably simplifies the calibration of the measurement tool for measuring radiation of a radiation system in that the photodiode, when being irradiated, gives off light visible to an operator of the calibration system. Furthermore, it is contemplated to use a photo detecting system for detecting light emitted from the photodiode elements when irradiated, for instance to facilitate an automatization of the calibration method. It should be understood that such a modification is within the scope of the invention.

Even though the present invention has been described with reference to specific exemplifying embodiments thereof, many different alterations, modifications and the like will become apparent for those skilled in the art. The described embodiments are therefore not intended to limit the scope of the present invention, as defined by the appended claims.

Furthermore, in the claims, the word "comprising" does not exclude other elements or steps, and the indefinite article "a" or "an" does not exclude plurality. Also, any reference signs in the claims should not be construed as limiting the scope of the present invention.

The invention claimed is:

1. A method for calibrating a measurement tool, including at least one photodiode element, for measuring the radiation in a radiation system, the system comprising a radiation generating unit capable of focusing the radiation to a fixed radiation focus point, the method comprising the step of:
    determining coordinates for a sensitive volume of said at least one photodiode element relative to a reference of a diode element holder of said measurement tool.

2. The method according to claim 1, further comprising the steps of:
    mounting said measurement tool in a positioning unit having a predetermined position relative to said radiation system, said positioning unit being capable of moving said measurement tool along three substantially orthogonal motional axes;
    calculating the coordinates for a sensitive volume of said at least one photodiode element relative to said positioning unit;
    controlling movements of said positioning unit so as to position said positioning unit in at least one measurement point corresponding to the calculated diode coordinates for said at least one photodiode element, wherein said sensitive volume of said at least one photodiode element is located substantially at said fixed focus point; and
    determining the position of the sensitive volume of said photodiode element relative to said focus point in each measurement point.

3. The method according to claim 2, wherein determining the position of the sensitive volume of said photodiode element relative to said focus point in each measurement point comprises:
    determining, in each measurement point and for each motional direction, whether there is a distance difference between said radiation focus point and said calculated respective diode coordinate; and
    if there is a distance difference in any of said motional directions, storing said coordinate distance difference as a calibration value for that photodiode element.

4. The method according to claim 3, wherein calculating the coordinates further comprises:
    determining a position for the diode element holder relative to said positioning unit.

5. The method according to claim 3, wherein mounting the measurement tool comprises:
    mounting said measurement tool in a fixation arrangement, said measurement tool being configured to be fixedly mounted in said fixation arrangement; and
    mounting said fixation arrangement in said positioning unit.

6. The method according to claim 2, wherein calculating the coordinates further comprises:
    determining a position for the diode element holder relative to said positioning unit.

7. The method according to claim 6, wherein mounting the measurement tool comprises:
    mounting said measurement tool in a fixation arrangement, said measurement tool being configured to be fixedly mounted in said fixation arrangement; and
    mounting said fixation arrangement in said positioning unit.

8. The method according to claim 2, wherein mounting the measurement tool comprises:
    mounting said measurement tool in a fixation arrangement, said measurement tool being adapted to be fixedly mounted in said fixation arrangement; and
    mounting said fixation arrangement in said positioning unit.

9. A calibration system for calibrating a measurement tool for measuring radiation in a radiation system, the radiation system comprising a radiation generating unit capable of focusing the radiation to a fixed radiation focus point, wherein the calibration system includes:
    a measurement tool, including at least one photodiode element; and
    a control unit;
    wherein the control unit is configured to determine coordinates for a sensitive volume of said at least one photodiode element relative to a reference of a diode element holder of said measurement tool.

10. The calibration system according to claim 9, wherein the radiation system further comprises a positioning unit having a predetermined position relative to the radiation system, and wherein the measurement tool is adapted to be mounted in said positioning unit, and the positioning unit is capable of moving the measurement tool along three substantially orthogonal axes, wherein the control unit is further configured to:
   calculate the coordinates for a sensitive volume of the at least one photodiode element relative to the positioning unit;
   control the movements of the positioning unit so as to position the positioning unit in at least one measurement point corresponding to said calculated coordinates for a sensitive volume of the at least one photodiode element, wherein said sensitive volume of said at least one photodiode element is located substantially at the fixed radiation focus point; and
   determine the position of the sensitive volume of said photodiode element relative to the radiation focus point in each measurement point.

11. The calibration system according to claim 10, wherein the control unit comprises a storage means, and where the control unit is further configured to:
   determine, in each measurement point and for each motional direction, whether there is a distance difference between said radiation focus point and said calculated respective diode coordinate; and
   if there is a distance difference in any of said motional directions, store said coordinate distance difference as a calibration value for that photodiode element in the storage means.

12. The calibration system according to claim 10, wherein the control unit is further configured to:
   determine a position for the diode element holder relative to said positioning unit.

13. The calibration system according to claim 10, wherein the measurement tool is configured to be fixedly mounted in a fixation arrangement, and the fixation arrangement is configured to be mounted in the positioning unit.

14. The calibration system according to claim 10, wherein the measurement tool comprises at least two photodiode elements arranged such that each photodiode element of the at least two photodiode elements is, when mounted in said positioning unit, situated in one of the orthogonal planes defined by said three substantially orthogonal motional axes, wherein the at least two photodiode elements are arranged such that at least one photodiode element is situated in a first plane and at least one photodiode element is situated in a second plane.

15. The calibration system according to claim 10, wherein the measurement tool is rotatably mounted such that the measurement tool is rotatable about at least one rotation axis.

16. The calibration system according to claim 15, wherein the at least one rotation axis is one of said three substantially orthogonal motional axes.

17. The calibration system according to claim 9, wherein the at least one photodiode element is a PIN photodiode.

18. A measurement tool with a calibration system, wherein the measurement tool is configured to measure radiation in
   a radiation system, the radiation system comprising a radiation generating unit capable of focusing the radiation to a fixed radiation focus point, the measurement tool comprising:
      a holder; and
      at least one photodiode element arranged on the holder, and
   the calibration system calibrating the measurement tool, the calibration system comprising:
      a control unit,
         wherein the control unit is configured to determine coordinates for a sensitive volume of said at least one photodiode element relative to a reference of a diode element holder of said measurement tool.

19. The measurement tool with the calibration system according to claim 18, wherein the holder is a printed circuit board.

* * * * *

UNITED STATES PATENT AND TRADEMARK OFFICE
CERTIFICATE OF CORRECTION

PATENT NO.       : 8,653,444 B2                                                      Page 1 of 1
APPLICATION NO. : 13/120136
DATED            : February 18, 2014
INVENTOR(S)      : Minoz et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 204 days.

Signed and Sealed this

Twenty-ninth Day of September, 2015

Michelle K. Lee
*Director of the United States Patent and Trademark Office*